US012618836B2

(12) United States Patent
    Barry et al.

(10) Patent No.: US 12,618,836 B2
(45) Date of Patent: May 5, 2026

(54) METHOD AND SYSTEM OF MICROFLUIDIC IMMUNOASSAY USING MAGNETIC BEADS

(71) Applicant: CALIPER LIFE SCIENCES, INC., Hopkinton, MA (US)

(72) Inventors: Andrew Barry, Chelmsford, MA (US); Laurel Provencher, Hopkinton, MA (US); Seth Cohen, Westford, MA (US); I-Jane Chen, Alameda, CA (US); Jun Yan, Franklin, MA (US); Jingjing Wang, Framingham, MA (US)

(73) Assignee: Revvity Health Sciences, Inc., Waltham, MA (US)

( * ) Notice: Subject to any disclaimer, the term of this patent is extended or adjusted under 35 U.S.C. 154(b) by 538 days.

(21) Appl. No.: 17/104,967

(22) Filed: Nov. 25, 2020

(65) Prior Publication Data

US 2021/0080457 A1     Mar. 18, 2021

Related U.S. Application Data

(60) Division of application No. 15/830,777, filed on Dec. 4, 2017, now Pat. No. 10,877,032, which is a continuation of application No. 14/597,999, filed on Jan. 15, 2015, now Pat. No. 9,835,623.

(60) Provisional application No. 61/927,960, filed on Jan. 15, 2014.

(51) Int. Cl.
    *G01N 33/561* (2006.01)
    *G01N 33/53* (2006.01)
    *G01N 33/543* (2006.01)

(52) U.S. Cl.
    CPC ....... *G01N 33/561* (2013.01); *G01N 33/5302* (2013.01); *G01N 33/54326* (2013.01)

(58) Field of Classification Search
    None
    See application file for complete search history.

(56) References Cited

U.S. PATENT DOCUMENTS

| | | | |
|---|---|---|---|
| 5,395,498 A | 3/1995 | Gombinsky et al. | |
| 5,736,410 A | 4/1998 | Zarling et al. | |
| 6,074,827 A * | 6/2000 | Nelson ............. | G01N 27/44743 |
| | | | 536/25.4 |
| 6,534,013 B1 | 3/2003 | Kennedy | |
| 6,613,581 B1 | 9/2003 | Wada et al. | |
| 6,632,655 B1 | 10/2003 | Mehta et al. | |
| 8,263,022 B2 | 9/2012 | Hu | |
| 9,835,623 B2 * | 12/2017 | Barry ............... | G01N 33/54326 |
| 10,877,032 B2 * | 12/2020 | Barry ............... | G01N 33/54326 |
| 2002/0070113 A1 * | 6/2002 | Miles ............... | G01N 27/44773 |
| | | | 204/601 |
| 2003/0044843 A1 | 3/2003 | Tanaka et al. | |
| 2003/0129666 A1 | 7/2003 | Tanaka et al. | |
| 2006/0292647 A1 | 12/2006 | Green et al. | |

| | | | |
|---|---|---|---|
| 2007/0099200 A1 * | 5/2007 | Chow .................. | G01N 33/557 |
| | | | 435/6.19 |
| 2009/0018029 A1 | 1/2009 | Miao et al. | |
| 2009/0269767 A1 | 10/2009 | Soderlund et al. | |
| 2012/0013554 A1 | 1/2012 | Nam et al. | |
| 2012/0032904 A1 | 2/2012 | Moon et al. | |
| 2012/0135541 A1 | 5/2012 | Herr et al. | |
| 2012/0329040 A1 | 12/2012 | Herr et al. | |
| 2013/0078663 A1 | 3/2013 | Herr et al. | |

FOREIGN PATENT DOCUMENTS

| | | | | |
|---|---|---|---|---|
| CN | 2010041230 A2 | 4/2010 | | |
| CN | 102713640 A | 10/2012 | | |
| CN | 2012138882 A2 | 10/2012 | | |
| CN | 103097029 A | 5/2013 | | |
| CN | 105992948 A | 10/2016 | | |
| EP | 1007953 | * 12/2006 | .......... | G01N 27/447 |
| KR | 20100026270 A | 3/2010 | | |
| WO | WO 2009108260 | * 9/2009 | | |

OTHER PUBLICATIONS

Kaneta et al. "On-column capture of a specific protein in capillary electrophoresis using magnetic beads" Electrophoresis 2006, 27, 3218-3223.

Kaneta et al. "On-column capture of a specific protein separated by SDS-CGE using an immunological reaction on magnetic beads" Electrophoresis 2007, 28, 2262-2266.

Huang, et al. "Solid-Phase purification of gene synthesis products using magnetic beads", SPIE, PO Box 10 Bellingham WA 98227-0010 USA, Jan. 1, 2008 (Jan. 1, 2008), XP0240446355.

International Search Report issued in corresponding international application No. PCT/US15/11659, Apr. 1, 2015.

International Preliminary Report on Patentability with Written Opinion issued in corresponding international application No. PCT/US15/11659, Apr. 1, 2015.

Notice of Allowance with listing of references, issued in corresponding U.S. Appl. No. 14/597,999, filed Aug. 8, 2017.

(Continued)

*Primary Examiner* — Ann Montgomery

(74) *Attorney, Agent, or Firm* — Day Pitney LLP; George Chaclas; Anthony A. Kassas

(57)     ABSTRACT

A microfluidic Western blot method and system including a microfluidic western blot method for immunoassay of proteins, the method including introducing a sample including the proteins onto a chip; electrophoretically separating the proteins; binding the separated proteins to beads to form protein-attached beads, the beads being magnetic; flowing the protein-attached beads into a magnetic holding region; applying a magnetic field to the magnetic holding region to fix the protein-attached beads in place within the magnetic holding region; binding primary antibodies to target proteins on the protein-attached beads; binding secondary antibodies to the bound primary antibodies; and detecting the bound secondary antibodies.

18 Claims, 8 Drawing Sheets

(56)            References Cited

OTHER PUBLICATIONS

CNIPA's first Office Action with Search Report, issued in corresponding Chinese patent application No. 2015800047674, Mar. 2018. (Original).

CNIPA's first Office Action, issued in corresponding Chinese patent application No. 2015800047674, Mar. 2018. (English language translation) (13 pages).

European Examination Report, issued in corresponding European patent application No. 15704409.0, Jun. 7, 2018. (5 pages).

Chetwynd et al. "Current Application of Capillary Electrophoresis in Nanomaterial Characterisation and Its Potential to Characterise the Protein and Small Molecule Corona", Nanomaterials 2018, 8, 99; doi:10.3390/nano8020099, pp. 1-29 (Year: 2018).

European Communication issued in corresponding application No. EP 15 704 409.0, Nov. 6, 2019. (4 pages).

Non-Final Office Action, issued in corresponding U.S. Appl. No. 15/830,777, filed Dec. 20, 2019. (16 pages).

Non-Final Office Action, issued in corresponding U.S. Appl. No. 15/830,777, filed May 20, 2020. (15 pages).

CNIPA's Notice on Reexamination, issued in corresponding Chinese patent application No. 201580004767.4, Oct. 21, 2020. (Original) (8 pages).

CNIPA's Notice on Reexamination, issued in corresponding Chinese patent application No. 201580004767.4, Oct. 21, 2020. (English language translation) (12 pages).

Extended Search Report in corresponding Application No. 22156907.2 dated Aug. 31, 2022, 9 pages.

CN Office Action corresponding to Application No. 202110788786.8, dated Oct. 7, 2023, 11 pages (translation unavailable).

CN Second Office Action corresponding to Application No. 202110788786.8, dated Jun. 1, 2024, 21 pages (with Machine Translation).

EP First Examination Report corresponding to Application No. 22156907.2, dated Aug. 29, 2024, 4 pages.

* cited by examiner

900

METHOD AND SYSTEM OF MICROFLUIDIC IMMUNOASSAY USING MAGNETIC BEADS

CROSS REFERENCE TO RELATED APPLICATIONS

This application is a divisional of and claims the benefit of priority to U.S. patent application Ser. No. 15/830,777 filed Dec. 4, 2017, which is a continuation of U.S. Ser. No. 14/597,999, issued U.S. Pat. No. 9,835,623, filed on Jan. 15, 2015, which claims the benefit of priority to U.S. Provisional Patent Application No. 61/927,960, filed Jan. 15, 2014. The entire disclosures of which are incorporated herein in their entirety, for any purpose whatsoever.

TECHNICAL FIELD

The technical field of this disclosure is assay systems, particularly, methods and systems of microfluidic immunoassay using magnetic beads.

BACKGROUND OF THE INVENTION

The use of microfluidic technology has been proposed for a number of analytical chemical and biochemical operations. This technology allows one to perform chemical and biochemical reactions, macromolecular separations, and the like, that range from the simple to the relatively complex, in easily automated, high-throughput, low-volume systems. Further information about microfluidic devices and systems is presented in U.S. Pat. No. 6,534,013 to Kennedy, issued Mar. 18, 2003, and incorporated in its entirety herein by reference.

As used herein, the term "microfluidic," or the term "microscale" when used to describe a fluidic element, such as a passage, chamber or conduit, generally refers to one or more fluid passages, chambers or conduits which have at least one internal cross-sectional dimension, e.g., depth or width, of between about 0.1 pm and 500 pm. In the devices of the present invention, the microscale channels preferably have at least one cross-sectional dimension between about 0.1 pm and 200 pm, more preferably between about 0.1 pm and 100 pm, and often between about 0.1 pm and 20 pm.

In general, microfluidic systems include a microfluidic device, or chip, that has networks of integrated submicron channels in which materials are transported, mixed, separated, and detected. Microfluidic systems typically also contain components that provide fluid driving forces to the chip and that detect signals emanating from the chip.

Microfluidic chips may be fabricated from a number of different materials, including glass or polymeric materials. An example of a commercially available microfluidic chip is the DNA LabChip® manufactured by Caliper Life Sciences, Inc. of Hopkinton, Massachusetts, and used with the Agilent 2100 Bioanalyzer system manufactured by Agilent Technologies, Inc. of Palo Alto, California. The chip has two major components: a working part made of glass, and a plastic caddy or mount bonded to the working part. The working part contains microfluidic channels in its interior, and wells on its exterior that provide access to the microfluidic channels. The working part is typically fabricated by bonding together two or more planar substrate layers. The microfluidic channels in the working part are formed when one planar substrate encloses grooves formed on another planar substrate. The mount protects the working part of the chip, and provides for easier handling of the chip by a user. The increased ease of handling partially results from the fact that the mount is larger than the working part of the device, which in many cases is too small and thin to be easily handled. The mount may be fabricated from any suitable polymeric material, such as an acrylic or thermoplastic. The glass working part is typically bonded to the polymeric mount using a UV-cured adhesive. Reservoirs in the mount provide access to the wells on the working part of the chip. The reservoirs hold much greater volumes of material than the wells in the working part, thus providing an interface between the macro-environment of the user and the microenvironment of the wells and channels of the microfluidic device.

This type of microfluidic chip is a "planar" chip. In a planar chip, the only access to the microchannels in the chip is through the reservoirs in the caddy and in-turn through the wells in the working part. Another type of microfluidic chip is a "sipper" chip, which has a small tube or capillary (the "sipper") extending from the chip through which fluids stored outside the chip can be directed into the microfluidic channels in the chip. Typical sipper chips have between one and twelve sippers. In use, the sipper is placed in a receptacle having sample material and minute quantities of the sample material are introduced, or "sipped" through the capillary tube to the microfluidic channels of the chip. This sipping process can be repeated to introduce any number of different sample materials into the chip. Sippers make it easier to carry out high-throughput analysis of numerous samples on a single microfluidic chip.

Western blot electrophoresis assays have been developed to detect specific proteins in a sample. The process can be divided into three parts: protein separation, sample transfer, and immunoassay. In protein separation, mechanical and/or chemical techniques are applied to a sample, such as a tissue sample, to expose proteins. The proteins are then separated with gel electrophoresis in which the speed of movement of the different proteins through the gel under a differential voltage is governed by the molecular weight of the individual proteins. In sample transfer, the separated proteins are moved from within the gel onto a membrane in a process called electroblotting, which uses electric current to move the proteins. In immunoassay, a primary antibody is attached to target proteins on the membrane, a secondary antibody is attached to the primary antibody, and a light emitter reacts with the secondary antibody to produce light at each of the target proteins. Detection of the light provides identification and quantification of the target proteins.

Although the current method of Western blot electrophoresis assay provides valuable results, the current method has a number of problems. The current method is a labor-intensive process, performed manually and requiring gel plates and special membrane paper to transfer the separated proteins. The manual nature of the process increases the cost and limits the number of samples which can be tested. A typical Western analysis requires between 8 and 24 hours of monitored operation, with almost half requiring hands-on, manual operation.

It would be desirable to have methods and systems of microfluidic immunoassay using magnetic beads that would overcome the above disadvantages.

SUMMARY OF THE INVENTION

One aspect of the invention provides a microfluidic Western blot method for immunoassay of proteins, the method including introducing a sample including the proteins onto a chip; electrophoretically separating the proteins; binding the separated proteins to beads to form protein-attached beads, the beads being magnetic; flowing the protein-attached beads into a magnetic holding region; applying a magnetic field to the magnetic holding region to fix the protein-attached beads in place within the magnetic holding region; binding primary antibodies to target proteins on the protein-attached beads; binding secondary antibodies to the bound primary antibodies; and detecting the bound secondary antibodies.

Another aspect of the invention provides a microfluidic western blot method for immunoassay of proteins, the method including providing a microfluidic chip having a substrate defining a sample well, a separation region operably coupled to the sample well, and a magnetic holding region operably coupled to the separation region; introducing a sample including the proteins into the sample well; flowing the sample into the separation region; applying a voltage across the separation region to electrophoretically separate the proteins in the separation region; binding the electrophoretically separated proteins to beads to form protein-attached beads, the beads being magnetic; flowing the protein-attached beads into the magnetic holding region; applying a magnetic field to the magnetic holding region to fix the protein-attached beads in place within the magnetic holding region; binding primary antibodies to target proteins on the protein-attached beads; binding secondary antibodies to the bound primary antibodies; and detecting the bound secondary antibodies.

Another aspect of the invention provides a microfluidic Western blot system for immunoassay of proteins with beads, the system including a microfluidic chip having a substrate defining a sample well, a separation region operably coupled to the sample well, and a magnetic holding region operably coupled to the separation region; and an electromagnet operably connected to provide a magnetic field to the magnetic holding region, the magnetic field being operable to fix the beads in place within the magnetic holding region.

Another aspect of the invention provides a microfluidic method for immunoassay of analytes, the method including resolving in a first fluid region one or more analytes in a sample disposed within the first fluid region based on size and charge of the one or more analytes; binding the resolved analytes to magnetic beads to form analyte-attached beads; applying a magnetic field to fix at least a portion of the analyte-attached beads in place; binding a detection reagent to the analyte-attached beads; and detecting the detection reagent.

The foregoing and other features and advantages of the invention will become further apparent from the following detailed description of the presently preferred embodiments, read in conjunction with the accompanying drawings. The detailed description and drawings are merely illustrative of the invention, rather than limiting the scope of the invention being defined by the appended claims and equivalents thereof.

BRIEF DESCRIPTION OF THE DRAWINGS

Like elements share like reference numbers between and among the various figures.

DETAILED DESCRIPTION

Figure 1:
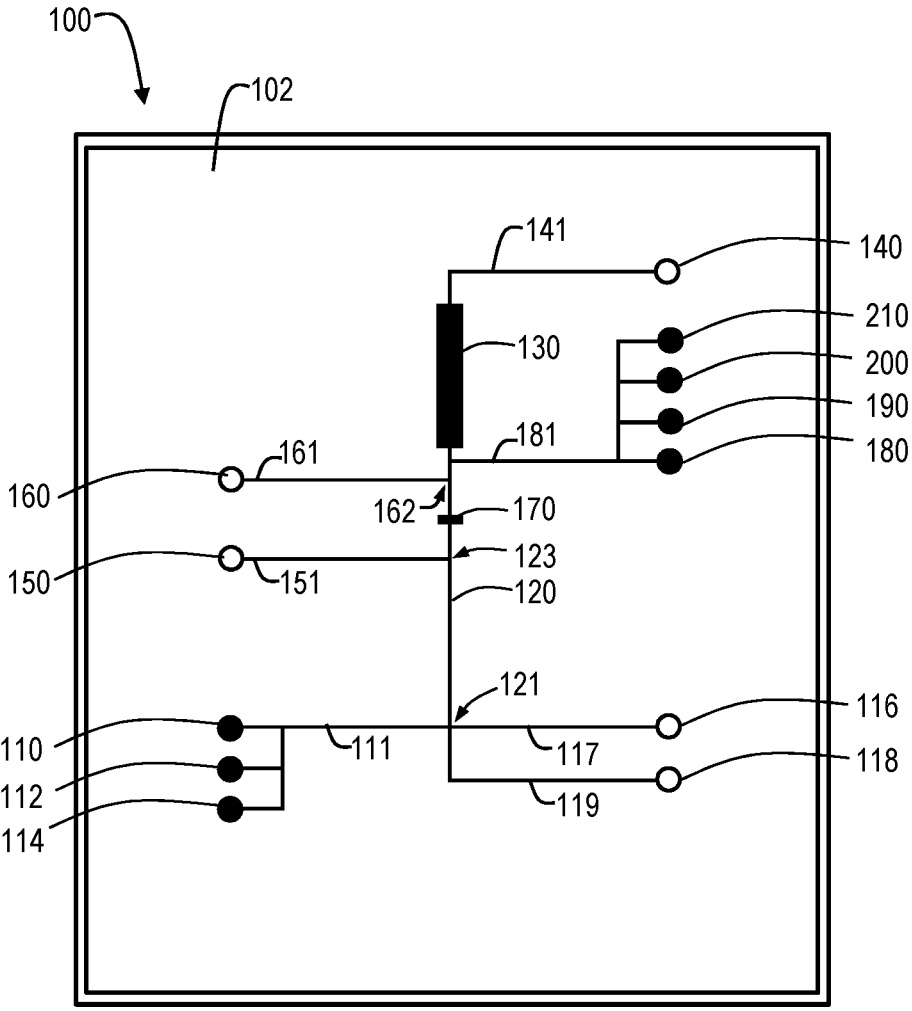
FIG. 1 is a schematic top view of one embodiment of a microfluidic Western blot device with multiple sample wells, separate destain and beads wells, and a detection reagent well made in accordance with the invention.

FIG. 1 is a schematic top view of one embodiment of a microfluidic Western blot device with multiple sample wells, separate destain and beads wells, and a detection reagent well made in accordance with the invention.

The microfluidic chip 100 has a substrate 102 which defines a number of wells and channels for performing a Western blot method of immunoassay. In this embodiment, the substrate 102 defines a sample well 110, a separation region 120 operably coupled to the sample well 110, and a magnetic holding region 130 operably coupled to the separation region 120.

The sample well 110 can be connected to the separation region 120 by a sample channel 111. The sample well 110 can also be operably connected to an injection electrode 116 through an injection channel 117 through the sample channel 111. In operation, the sample including the proteins can be flowed from the sample well 110 through the sample channel 111 into the injection channel 117 by applying a differential voltage between the sample well 110 and the injection electrode 116. The injection channel 117 can be operably connected to the first separation electrode channel 119. The sample can be flowed from the injection channel 117 to the first separation electrode channel 119 by applying a differential voltage between the injection electrode 116 and first separation electrode 118 operably connected to the first separation electrode channel 119. In one embodiment, the differential voltage used to move the proteins around the chip can be a high differential voltage, in contrast with a low differential voltage which can be used to move immunoassay chemicals through the magnetic holding region.

In this example, the microfluidic chip 100 includes a number of sample wells 110, 112, 114. The samples from the sample wells can be processed sequentially, i.e., the sample from sample well 110 can be processed first, followed by the sample from the sample well 112 and the sample well 114. Those skilled in the art will appreciate that the microfluidic chip 100 can include any number of sample wells as desired for a particular application.

The first separation electrode channel 119 can be operably connected to the separation region 120. The separation region 120 is primed with gel and dye so that electrophoresis can be performed on the sample in the separation region 120.

The separation region 120 can also be connected to a second separation electrode 140 through the magnetic holding region 130 and second separation electrode channel 141.

Electrophoresis can be performed on the sample by applying a differential voltage between the first separation electrode 118 and the second separation electrode 140. Electrophoresis separates the proteins in the sample into one or more protein peaks as the lower molecular weight proteins move more quickly than the heavier molecular weight proteins through the gel of the separation region 120 between the downstream end 121 and the upstream end 123. The differential voltage between the first separation electrode 118 and the second separation electrode 140 can also be used to move the sample from the separation region 120 to the magnetic holding region 130.

A destain well 150 can be operably connected to the downstream end 123 of the separation region 120 through a destain channel 151 to add destaining solution to the separated sample leaving the separation region 120. The destaining solution removes detergent (SDS) micelles to allow visualization of protein peaks in the sample and reduce signal background. The destaining solution can be flowed into the sample by applying a differential voltage between an electrode associated with the destain well 150 and the second separation electrode 140.

A peak detection region 170 can be provided between the separation region 120 and the magnetic holding region 130. A peak optical detector (not shown) monitoring the peak detection region 170 can detect the protein peaks in the sample moving through the peak detection region 170, which can be used to detect when the last protein peak enters the magnetic holding region 130.

A bead well 160 can be operably connected to the downstream end of the peak detection region 170 through a bead channel 161 to add beads to the separated sample leaving the peak detection region 170. The surfaces of the beads are functionalized to attach to any and all proteins in the sample to form protein-attached beads. Further, the beads are magnetic and can be magnetically manipulated within the magnetic holding region 130. In one embodiment, the beads can be primary antibody attached beads, i.e., a bead with a primary antibody attached to the bead at the time of manufacture and before the bead is introduced onto the chip. Exemplary beads are available from PerkinElmer chemagen Technologie GmbH of Baesweiler, Germany. In one embodiment, the beads can be nanobeads. The beads can be flowed into the sample by applying a differential voltage between an electrode associated with the bead well 160 and the second separation electrode 140.

An immunoassay channel 181 can be attached downstream of the bead channel 161 and before the magnetic holding region 130 to allow addition of immunoassay chemicals. In this example, the immunoassay channel 181 is operably connected to a blocking buffer well 180, a primary antibody well 190, a secondary antibody well 200, and a detection reagent well 210. When differential voltage between the first separation electrode 118 and the second separation electrode 140 is used to move the sample into the magnetic holding region 130, the differential voltage can be turned off before the immunoassay chemicals are added.

In operation, when the last protein peak enters the magnetic holding region 130, the differential voltage between the first separation electrode 118 and the second separation electrode 140 can be turned off and an electromagnet (not shown) operably connected to the magnetic holding region 130 can be energized to fix the protein-attached beads in place within the magnetic holding region 130. In one example, the magnetic field is generated by a circular electromagnet maintaining the protein-attached beads dispersed across the capillary section within the magnetic holding region 130.

The immunoassay chemicals from each of the blocking buffer well 180, primary antibody well 190, secondary antibody well 200, and detection reagent well 210 can be flowed through the magnetic holding region 130 to contact the protein-attached beads in turn by applying a differential voltage between an electrode associated with each of the wells and the second separation electrode 140. The magnetic holding region 130 can be washed between application of each of the immunoassay chemicals as desired for a particular application by applying a differential voltage between an electrode associated with the destain well 150 and the second separation electrode 140. Each of the immunoassay chemicals can be allowed to incubate within the magnetic holding region 130 to provide a desired incubation time and/or temperature as desired for a particular application by removing the differential voltage between the electrode associated with each of the wells and the second separation electrode 140 after one of the immunoassay chemicals has been flowed into the magnetic holding region 130.

A blocking buffer can be flowed into the magnetic holding region 130 by applying a differential voltage between an electrode associated with the blocking buffer well 180 and the second separation electrode 140. The blocking buffer is used after protein binding to the beads to saturate all remaining protein binding sites of the beads and prevent non-specific immunoassay reagents binding to the beads. Those skilled in the art will appreciate that the immunoassay can be performed without use of a blocking buffer as desired for a particular application. Any unbound blocking buffer can be washed from the magnetic holding region 130 by applying a differential voltage between the electrode associated with the destain well 150 and the second separation electrode 140.

A primary antibody can be flowed into the magnetic holding region 130 by applying a differential voltage between an electrode associated with the primary antibody well 190 and the second separation electrode 140. The primary antibody binds with target proteins on the protein-attached beads. Any unbound primary antibody can be washed from the magnetic holding region 130 by applying a differential voltage between the electrode associated with the destain well 150 and the second separation electrode 140. In one example, the microfluidic chip 100 includes a heating element (not shown) operably connected to the magnetic holding region 130 to incubate the primary antibody on the protein-attached beads at a temperature as desired for a particular application.

A secondary antibody can be flowed into the magnetic holding region 130 by applying a differential voltage between an electrode associated with the secondary antibody well 200 and the second separation electrode 140. The secondary antibody binds with the primary antibody bound to the protein-attached beads. Any unbound secondary antibody can be washed from the magnetic holding region 130 by applying a differential voltage between the electrode associated with the destain well 150 and the second separation electrode 140.

A detection reagent can be flowed into the magnetic holding region 130 by applying a differential voltage between an electrode associated with the detection reagent well to 10 and the second separation electrode 140. The detection reagent reacts with the secondary antibody bound to the primary antibody, which is bound to the target protein.

In one example, the secondary antibody includes a coupled enzyme (such as horseradish peroxidase HRP, for example) and the detection reagent is an enzyme substrate (such as horseradish peroxidase tyramide signal amplification HRP/TSA, for example) which reacts with the coupled enzyme and generates light.

An immunoassay optical detector (not shown) can be used to detect light from the secondary antibodies. In one embodiment, the immunoassay optical detector is operably connected to receive light from the magnetic holding region 130 when the protein-attached beads are fixed in place within the magnetic holding region 130. The magnetic field in the magnetic holding region 130 can be released after the light is measured and the sample can be removed from the microfluidic chip 100. In another embodiment, the immunoassay optical detector is operably connected to receive light from the protein-attached beads as the protein-attached beads flow past the immunoassay optical detector within the magnetic field in the magnetic holding region 130 has been released and a differential voltage has been applied between the first separation the electrode 118 and the second separation electrode 140.

A waste well can be associated with the second separation electrode 140 so that the sample can be removed from the microfluidic chip 100 by application of a differential voltage between the first separation the electrode 118 and the second separation electrode 140. In one embodiment, another sample, such as a sample from the second sample well 112, can be tested after the first sample is removed from the chip. In another embodiment, another sample, such as a sample from the second sample well 112, can be moved into the separation region 120 at the same time that the first sample is being removed from the chip.

Those skilled in the art will appreciate that the microfluidic chip 100 can be adapted as desired for a particular application. In one embodiment, one or more of the separation region 120, the peak detection region 170, and/or the magnetic holding region 130 is a channel. In another embodiment, one or more of the separation region 120, the peak detection region 170, and/or the magnetic holding region 130 is a chamber. The driving force moving the sample through the microfluidic chip 100 can be differential voltage and/or differential pressure along the channels. The microfluidic chip 100 can be adapted for use in performing other types of immunoassays.

The immunoassay chemicals can also be selected as desired for a particular application. In one embodiment, the primary antibody binds with a single target protein and the immunoassay optical detector receives light at a single wavelength to identify and quantify the single target protein. In another embodiment, multiplexing can be performed on a single chip, where the primary antibody is a mixture of antibodies that bind with different target proteins and are associated with different secondary antibodies. The difference secondary antibodies can generate light at different wavelengths, so that more than one target protein can be identified and quantified at one time when receiving light from the magnetic holding region at the immunoassay optical detector.

FIGS. 2-7 illustrate various combinations of the elements of different microfluidic Western blot devices. Those skilled in the art will appreciate that the various elements can be provided in different combinations as desired for a particular application.

Figure 2:
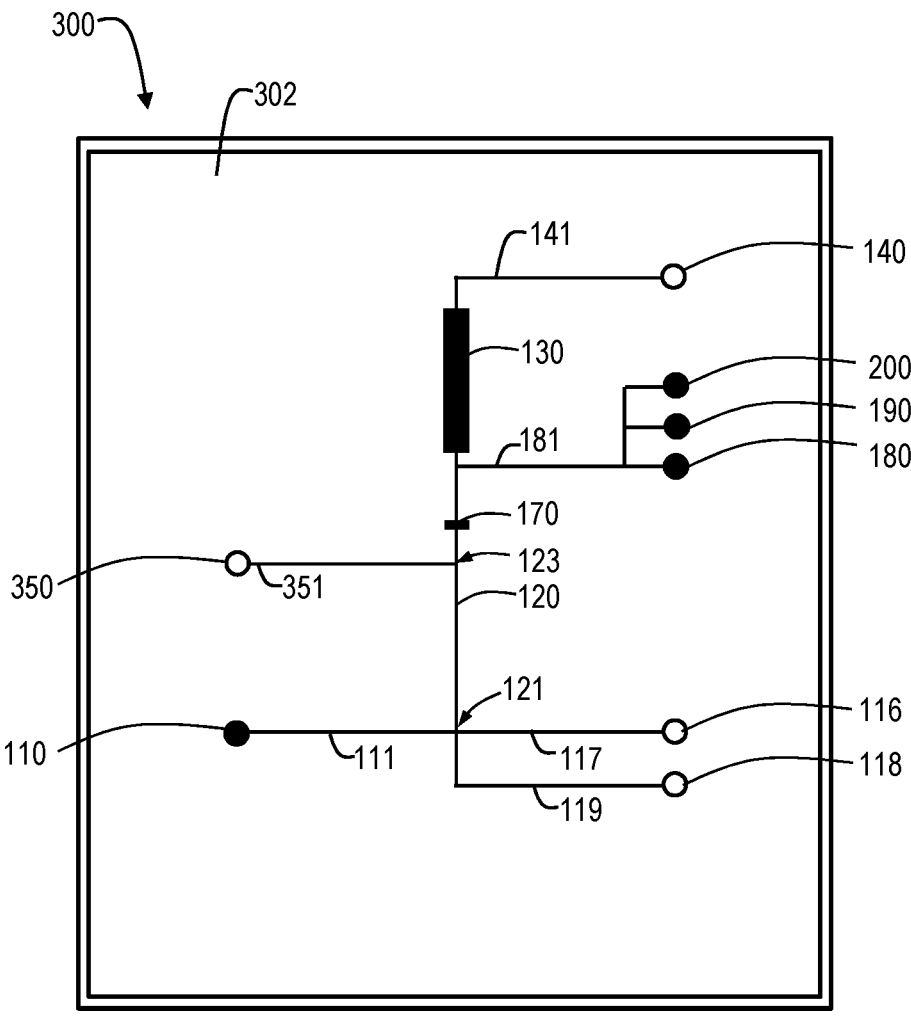
FIG. 2 is a schematic top view of one embodiment of a microfluidic Western blot device with a combined destain and bead well made in accordance with the invention.

FIG. 2 is a schematic top view of one embodiment of a microfluidic Western blot device with a combined destain and bead well made in accordance with the invention. In this embodiment, the microfluidic chip 300 has a substrate 302 which forms a destain/bead well 350 operably connected to the downstream end 123 of the separation region 120 through a destain/bead channel 351 to add a mixture of the destaining solution and beads to the separated sample leaving the separation region 120. The mixture of destaining solution and beads can be used to wash the immunoassay chemicals (blocking buffer, primary antibodies, secondary antibodies) from the magnetic holding region. This embodiment includes a single sample well 110 rather than multiple sample well and omits the detection reagent well connected to the immunoassay channel 181.

Figure 3:
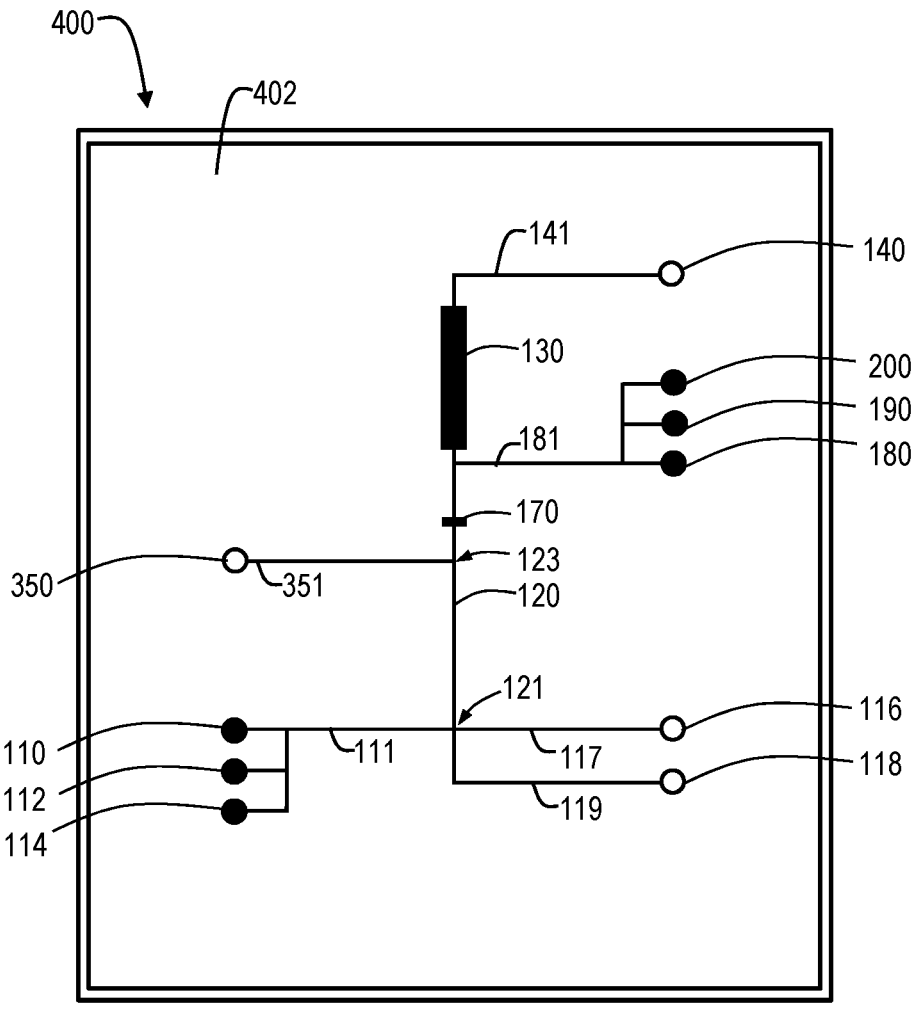
FIG. 3 is a schematic top view of one embodiment of a microfluidic Western blot device with multiple sample wells and a combined destain and bead well made in accordance with the invention.

FIG. 3 is a schematic top view of one embodiment of a microfluidic Western blot device with multiple sample wells and a combined destain and bead well made in accordance with the invention. In this embodiment, the microfluidic chip 400 has a substrate 402 which forms a destain/bead well 350 operably connected to the downstream end 123 of the separation region 120 through a destain/bead channel 351 to add a mixture of the destaining solution and beads to the separated sample leaving the separation region 120. This embodiment includes a multiple sample wells 110, 112, 114 and omits the detection reagent well connected to the immunoassay channel 181.

Figure 4:
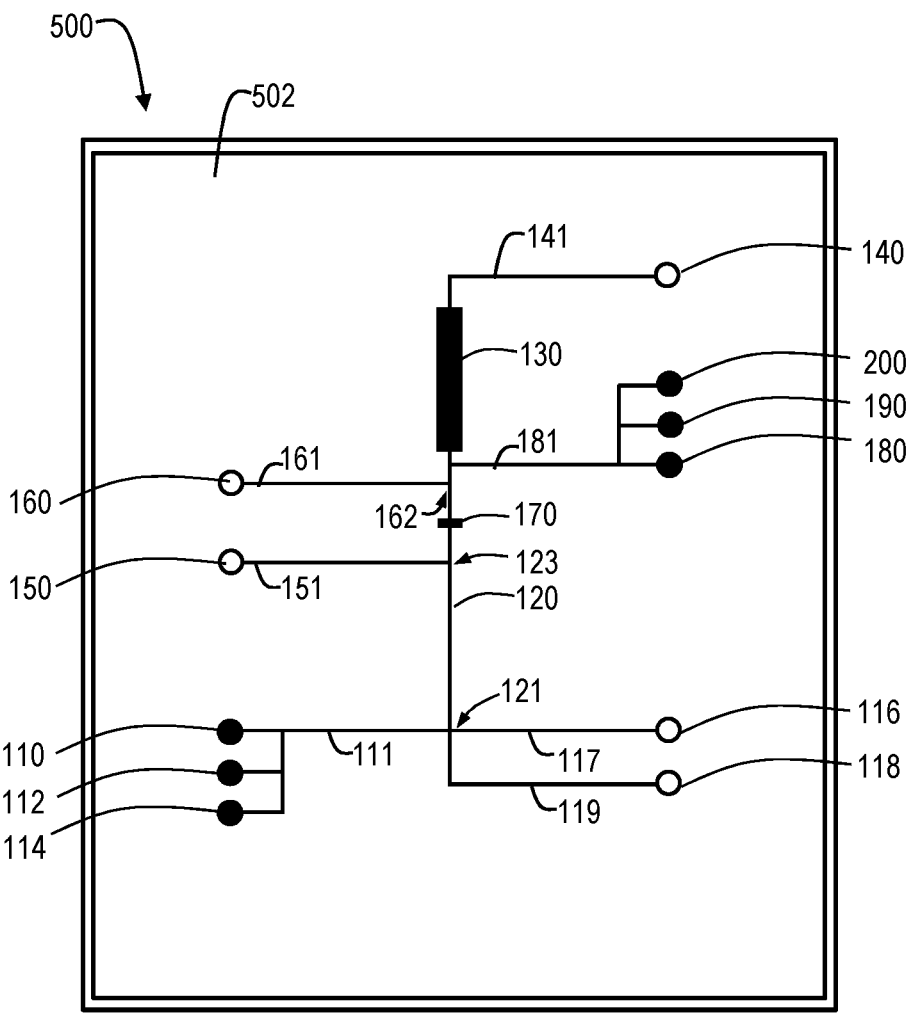
FIG. 4 is a schematic top view of one embodiment of a microfluidic Western blot device with multiple sample wells and separate destain and bead wells made in accordance with the invention.

FIG. 4 is a schematic top view of one embodiment of a microfluidic Western blot device with multiple sample wells and separate destain and bead wells made in accordance with the invention. In this embodiment, the microfluidic chip 500 has a substrate 502 which forms multiple sample wells 110, 112, 114. This embodiment includes a separate destain well 150 and bead well 160, to avoid bead in the peak detection region 170 and beads in the destaining solution used to wash the immunoassay chemicals (blocking buffer, primary antibodies, secondary antibodies) from the magnetic holding region. This embodiment also omits the detection reagent well connected to the immunoassay channel 181.

Figure 5:
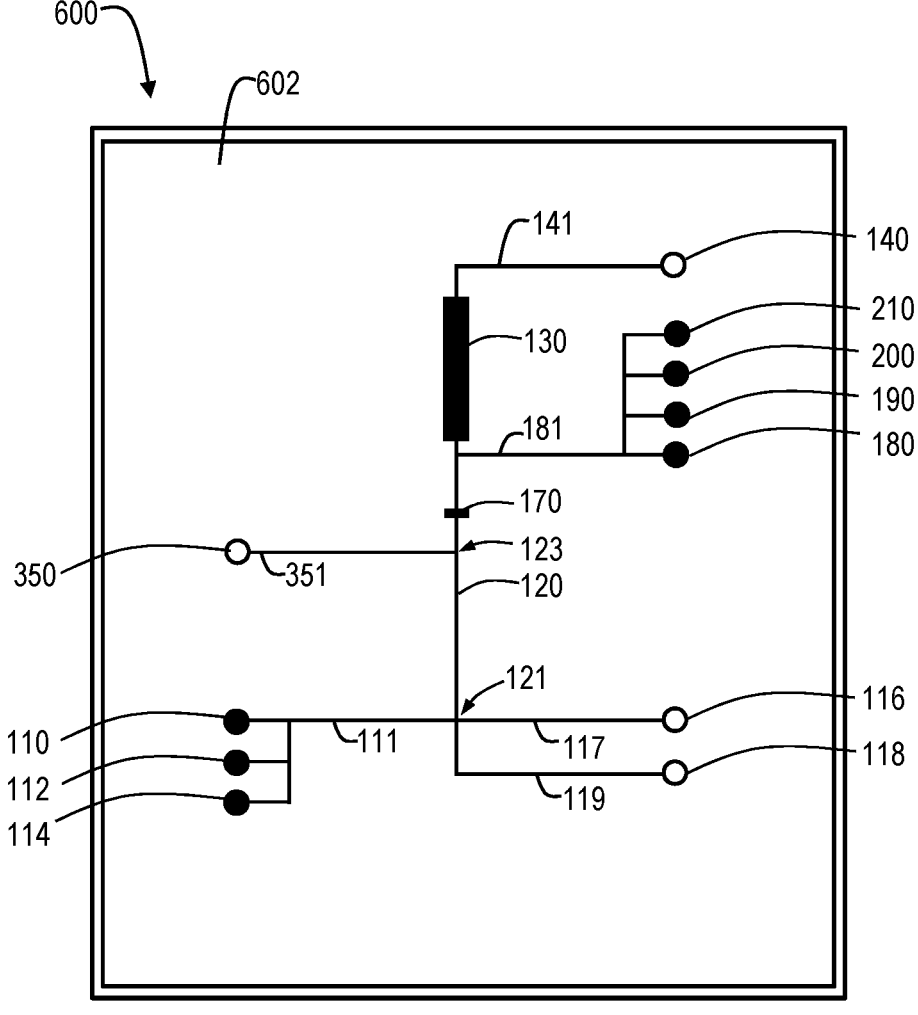
FIG. 5 is a schematic top view of one embodiment of a microfluidic Western blot device with multiple sample wells, a combined destain and bead well, and a detection reagent well made in accordance with the invention.

FIG. 5 is a schematic top view of one embodiment of a microfluidic Western blot device with multiple sample wells, a combined destain and bead well, and a detection reagent well made in accordance with the invention. In this embodiment, the microfluidic chip 600 has a substrate 602 which forms multiple sample wells 110, 112, 114. This embodiment includes a destain/bead well 350 operably connected to the downstream end 123 of the separation region 120 through a destain/bead channel 351 to add a mixture of the destaining solution and beads to the separated sample leaving the separation region 120. This embodiment also includes the detection reagent well to 10 operably connected to the immunoassay channel 181.

Figure 6:
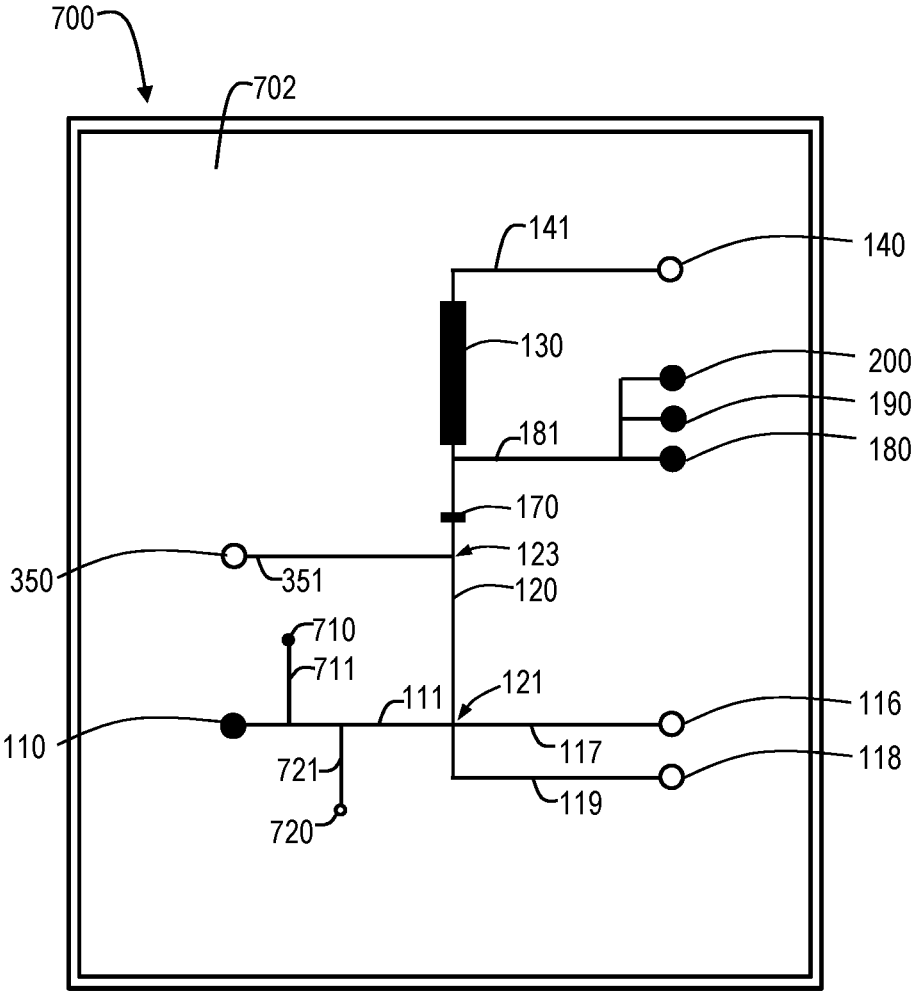
FIG. 6 is a schematic top view of one embodiment of a microfluidic Western blot device with a sample sipper made in accordance with the invention.

FIG. 6 is a schematic top view of one embodiment of a microfluidic Western blot device with a sample sipper made in accordance with the invention. In this embodiment, the microfluidic chip 700 has a substrate 702 which forms a low-pressure port 710 operably connected to the sample channel 111 by a low-pressure port channel 711 and a sipper port 720 operably connected to the sample channel 111 by a sipper port channel 721. In operation, the low-pressure port 710 is held at a lower pressure than the sipper port 720, which has been introduced into a sample well of a well plate (not shown), such as a 96-well plate or the like. The sample contained in the well plate is drawn into the sample channel 111 through the sipper port 720. In this example, multiple samples from the well plate can be processed through the microfluidic chip 700 using the same immunoassay chemicals from the blocking buffer well 180, the primary antibody well 190, and the secondary antibody well 200.

Figure 7:
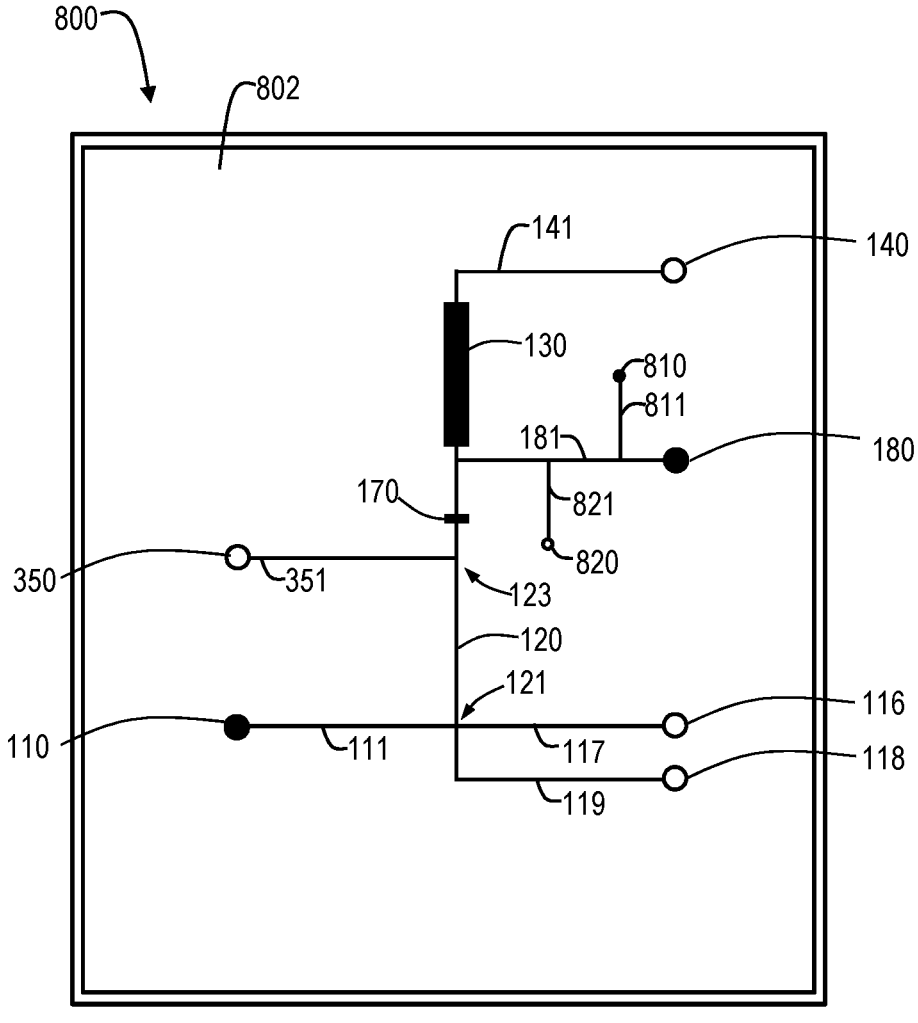
FIG. 7 is a schematic top view of one embodiment of a microfluidic Western blot device with an antibody sipper made in accordance with the invention.

FIG. 7 is a schematic top view of one embodiment of a microfluidic Western blot device with an antibody sipper made in accordance with the invention. In this embodiment, the microfluidic chip 800 has a substrate 802 which forms a low-pressure port 810 operably connected to the immuno-assay channel 181 by a low-pressure port channel 811 and a sipper port 820 operably connected to the immunoassay channel 181 by a sipper port channel 821. In operation, the low-pressure port 810 is held at a lower pressure than the sipper port 820, which has been introduced into an antibody well of a well plate (not shown), such as a 96-well plate or the like. The antibody contained in the well plate is drawn into the immunoassay channel 181 through the sipper port 820. In this example, multiple antibodies from the well plate can be processed through the microfluidic chip 800 using the same sample from the sample well 110.

Figure 8:
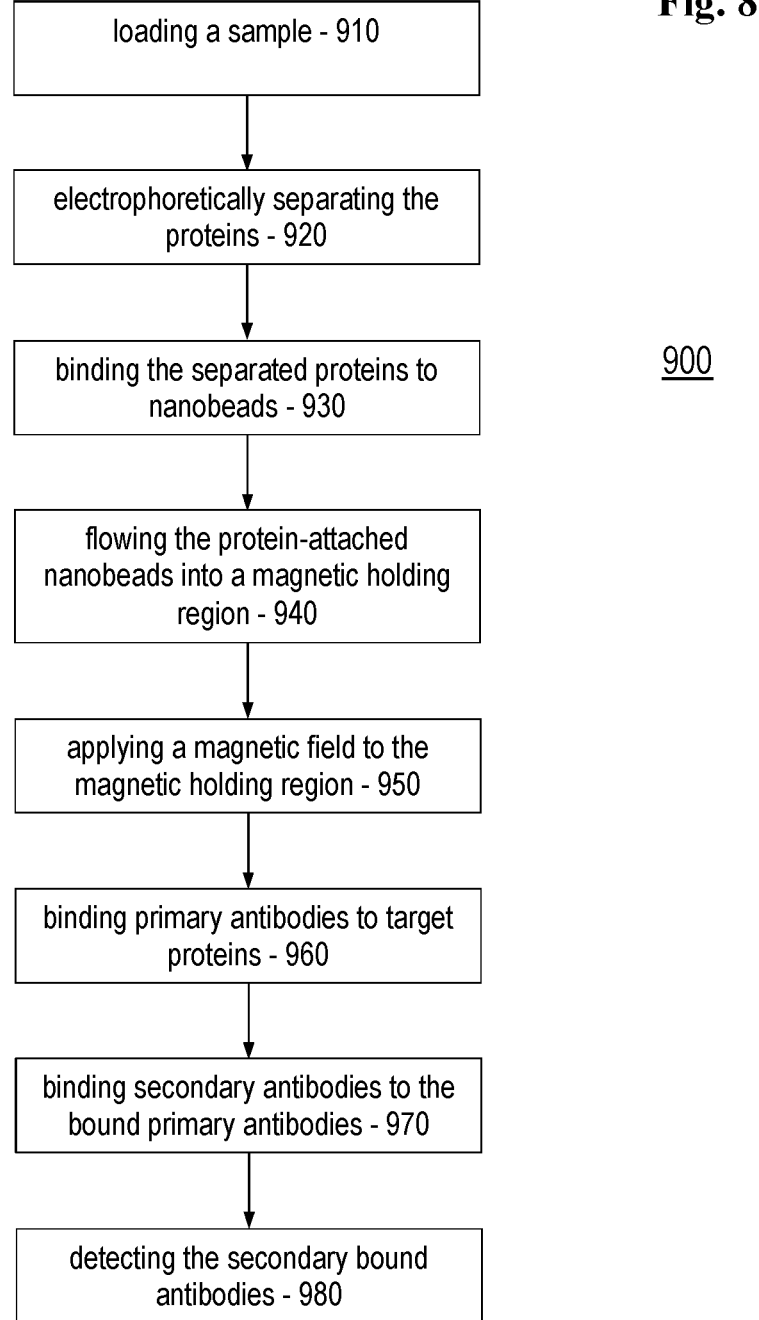
FIG. 8 is a flow chart of a microfluidic Western blot method in accordance with the invention.

FIG. 8 is a flow chart of a microfluidic Western blot method in accordance with the invention. The microfluidic Western blot method 900 for immunoassay of proteins includes introducing a sample 910 including the proteins onto a chip; electrophoretically separating the proteins 920; binding the separated proteins to beads 930 to form protein-attached beads, the beads being magnetic; flowing the protein-attached beads into a magnetic holding region 940; applying a magnetic field to the magnetic holding region 950 to fix the protein-attached beads in place within the magnetic holding region; binding primary antibodies to target proteins 960 on the protein-attached beads; binding secondary antibodies to the bound primary antibodies 970; and detecting the bound secondary antibodies 980. The method 900 can be performed using a microfluidic chip having a substrate defining a sample well, an separation region operably coupled to the sample well, and a magnetic holding region operably coupled to the separation region, as illustrated in FIGS. 1-7.

Referring to FIG. 8, introducing a sample 910 including the proteins onto a chip moves the sample into position to perform the Western blot method. In one embodiment, the sample can be loaded by applying a differential voltage between electrodes on the chip. In another embodiment, the sample can be loaded by applying a differential pressure between ports on the chip. Those skilled in the art will appreciate that the sample can be loaded in any way desired for a particular application. In one embodiment, the method 900 can include priming the chip with gel and dye before the introducing 910.

Electrophoretically separating the proteins 920 can include applying a differential voltage to separate the proteins in the sample into one or more protein peaks as the lower molecular weight proteins move more quickly than the heavier molecular weight proteins through the gel of a separation region on the chip.

Binding the separated proteins to beads 930 to form protein-attached beads attaches substantially all of the separated proteins in the sample to the beads. The beads are magnetic, so the protein-attached beads can be moved by a magnetic field. In one embodiment, the binding the separated proteins to beads 930 can include destaining the proteins before binding the separated proteins to the beads. The electrophoretically separating the proteins 920 can then further include detecting migrating peaks in the destained proteins. The flowing the protein-attached beads into a magnetic holding region 940 can then further include flowing the protein-attached beads into the magnetic holding region until a last one of the migrating peaks is detected at which point all of the protein-attached beads will be in the magnetic holding region.

Flowing the protein-attached beads into a magnetic holding region 940 places the protein-attached beads in position in the magnetic holding region for immunoassay. In one embodiment, the protein-attached beads can flow from applying a differential voltage between electrodes on the chip. In another embodiment, the protein-attached beads can flow from applying a differential pressure between ports on the chip. Those skilled in the art will appreciate that the protein-attached beads can be made to flow into a magnetic holding region in any way desired for a particular application.

Applying a magnetic field to the magnetic holding region 950 to fix the protein-attached beads in place within the magnetic holding region holds the protein-attached beads in place during the immunoassay. In one example, the magnetic field from an electromagnet can hold the protein-attached beads to the base of the magnetic holding region. The magnetic field also can preserve the relative position of the protein peaks of the sample within the magnetic holding region.

Binding primary antibodies to target proteins 960 on the protein-attached beads tags the target proteins for detection while leaving proteins which are not of interest untagged. In one embodiment, the binding primary antibodies to target proteins 960 can include incubating the primary antibodies on the protein-attached beads and washing unbound primary antibodies from the magnetic holding region. In another embodiment, the method 900 can include flowing blocking buffer through the magnetic holding region over the protein-attached beads before the binding primary antibodies. The method 900 can then further include incubating the blocking buffer on the protein-attached beads and washing unbound blocking buffer from the magnetic holding region.

Binding secondary antibodies to the bound primary antibodies 970 tags the bound primary antibodies with the secondary antibodies to be used in identifying the bound primary antibodies, which are attached to the target proteins. In one embodiment, the binding secondary antibodies to the bound primary antibodies 970 can include washing unbound secondary antibodies from the magnetic holding region.

Detecting the bound secondary antibodies 980 can provide an indication of the target proteins in the sample, since the bound secondary antibodies are attached to the bound primary antibodies, which are attached to the target proteins. In one embodiment, the method 900 includes flowing detection reagent through the magnetic holding region over the protein-attached beads before the detecting 980 and the detecting the bound secondary antibodies 980 includes detecting light emitted from reaction of the detection reagent with the bound secondary antibodies.

The detecting the bound secondary antibodies 980 can be performed with the sample in the magnetic holding region or as the sample flows from the magnetic holding region. In one embodiment, the detecting 980 can include detecting the bound secondary antibodies in the magnetic holding region with the magnetic field applied to the magnetic holding region. In another embodiment, the method 900 can include releasing the magnetic field in the magnetic holding region to release the protein-attached beads. The detecting 980 can then include detecting the bound secondary antibodies flowing by a stationary detector.

The method 900 can continue with emptying the magnetic holding region and/or introducing a new sample for analysis. In one embodiment, the method 900 can include releasing the magnetic field in the magnetic holding region to release the protein-attached beads. The method 900 can further include introducing a second sample onto the chip and performing a Western blot analysis on the second sample as desired. In one embodiment, the second sample can be tested after the first sample is removed from the chip. In another embodiment, the second sample can be electrophoretically separated at the same time that the first sample is being removed from the chip. Washes of the chip can be provided between sequential samples to prevent cross contamination as desired for a particular application.

It is important to note that FIGS. 1-8 illustrate specific applications and embodiments of the invention, and are not intended to limit the scope of the present disclosure or claims to that which is presented therein. Upon reading the specification and reviewing the drawings hereof, it will become immediately obvious to those skilled in the art that myriad other embodiments of the invention are possible, and that such embodiments are contemplated and fall within the scope of the presently claimed invention. The examples above deal primarily with Western blot immunoassay of proteins on a chip using magnetic nanobeads, but those skilled in the art will appreciate that the method and system of microfluidic immunoassay using magnetic beads can be applied equally well to immunoassay of any analytes on a chip using magnetic beads.

While the embodiments of the invention disclosed herein are presently considered to be preferred, various changes and modifications can be made without departing from the spirit and scope of the invention. The scope of the invention is indicated in the appended claims, and all changes that come within the meaning and range of equivalents are intended to be embraced therein.

We claim:

1. A microfluidic Western blot system for immunoassay of analytes in a sample, the system including a microfluidic chip comprising:

a sample well configured to hold the sample;

a sample channel in fluid communication with the sample well and configured to supply the sample to the system;

an injection channel in fluid communication with the sample channel and configured to draw the sample from the sample well through the sample channel into the injection channel by applying a differential voltage between a sample well electrode and an injection electrode disposed downstream of the injection channel;

a first separation electrode channel in fluid communication with the sample channel and the injection channel, the first separation electrode channel is configured to draw the sample from the injection channel into the first separation electrode channel by applying a differential voltage between the injection electrode and a first separation electrode disposed downstream of the first separation electrode channel;

a separation region in fluid communication with, and downstream of, the sample well, the sample channel, the injection channel, and the first separation electrode channel, wherein the sample channel, the injection channel, and the first separation electrode channel are all operably connected together at an upstream end of the separation region at a common, non-linear junction, the channels being electrically discrete and individually addressable by the sample-well electrode, the injection electrode, and the first separation electrode, such that independent voltage control at the electrodes selectively routes a discrete plug of the sample among the channels without electrical cross-talk, the injection electrode being positioned intermediate the sample well and the first separation electrode to establish a progressive voltage gradient through the junction during sample transfer the separation region is configured to draw the sample from the first separation electrode channel into the separation region and electrophoretically separate analytes in the sample within the separation region based on size and charge by applying a differential voltage between the first separation electrode and a second separation electrode disposed downstream of the separation region;

a peak detection microfluidic channel disposed downstream of the separation region and upstream of a bead well, the peak detection microfluidic channel defining an optically accessible portion of the microfluidic chip configured to permit detection of fluorescent or luminescent optical signals from the separated analytes migrating from the separation region, the peak detection microfluidic channel enabling measurement of migration times and signal intensities of the separated analytes corresponding to analyte size and concentration and enabling generation of data for quantitative analysis of the separated analytes and for timing control of subsequent electrophoretic transfer toward the bead well;

a bead well in fluid communication with, and downstream of, the separation region, the bead well disposed upstream of the second separation electrode, the bead well is configured to supply magnetic beads for attachment to the separated analytes to form protein-attached magnetic beads, the bead well is configured to supply the magnetic beads for attachment by applying a differential voltage between an electrode associated with the bead well and the second separation electrode;

a magnetic holding region in fluid communication with, and downstream of, the separation region and the bead well, the magnetic holding region being electrically isolated from the separation region to prevent electrophoretic migration during immunoassay incubation, and operably coupled to an electromagnet oriented to induce a magnetic field orthogonal to the electrophoretic flow direction within the magnetic holding region, the electromagnet is configured to fix the protein-attached magnetic beads in place within the magnetic holding region, the first and second separation electrodes are configured to move the separated analytes from the separation region to the magnetic holding region by applying a differential voltage between the first and second separation electrodes; and an antibody well in fluid communication with, and upstream of, the magnetic holding region and second separation electrode, the antibody well is configured to flow antibodies into the magnetic holding region via an immunoassay channel for binding to the protein-attached beads by applying a differential voltage between an electrode associated with the antibody well and the second separation electrode.

2. The system of claim 1, wherein the antibody well is configured to hold either primary or secondary antibodies, and further comprising: a second antibody well configured to hold the other of primary or secondary antibodies, wherein the immunoassay channel is configured to supply primary antibodies or secondary antibodies to the magnetic holding channel for binding to the protein-attached magnetic beads.

3. The system of claim 1, further comprising a blocking buffer well and a detection reagent well, wherein the immunoassay channel is configured to supply blocking buffer or detection reagent to the magnetic holding channel for binding to the protein-attached magnetic beads.

4. The system of claim 1, further comprising a destain well operably coupled to, and downstream of, the separation region, the destaining well is configured to add destaining solution to the separated analytes in sample to remove detergent micelles, allowing visualization of protein peaks in the sample and reducing signal background upon detection, the destain well is configured to add destaining solution by applying a differential voltage between an electrode associated with the destain well and the second separation electrode.

5. The system of claim 1, further comprising a heating element operably coupled to the magnetic holding region to control temperature for incubation within the magnetic holding region.

6. The system of claim 1, further comprising a sipper port operably coupled to the sample well for automating liquid sampling.

7. The system of claim 1, wherein the upstream end of the separation region connecting together all of the sample channel, the injection channel, and the first separation electrode channel is configured to draw the sample non-linearly (i) from the sample channel into the injection channel, (ii) from the injection channel into the separation electrode channel; and (iii) from the separation electrode channel into the separation region.

8. The system of claim 1, wherein the first separation electrode, second separation electrode, and injection electrode are positioned non-linearly such that:

the injection channel is configured to draw the sample from the sample well, through the sample channel, to the upstream end of the separation region, and subsequently into the injection channel, the first separation electrode channel is configured to draw the sample from the injection channel, back to the upstream end of the separation region, and subsequently into the first separation electrode channel, and the separation region is configured to draw the sample from the first separation electrode channel, back to the upstream end of the separation region, and subsequently into the separation region.

9. The system of claim 1, further comprising a control circuit operably coupled to the electrodes associated with the sample well, injection channel, first separation electrode channel, and separation region, the control circuit is configured to receive data from the peak detection microfluidic channel and to automatically adjust the applied voltages to maintain uniform electrophoretic separation and timed transfer of the separated analytes toward the bead well.

10. The system of claim 1, further comprising a wash-buffer well in fluid communication with the magnetic holding region, the wash-buffer well is configured to deliver buffer solution by electrophoretic or electroosmotic flow between an electrode associated with the wash-buffer well and the second separation electrode to remove unbound reagents from the protein-attached magnetic beads before antibody incubation.

11. The system of claim 1, wherein the magnetic holding region comprises a plurality of discrete sub-regions, each associated with a different antibody well and electromagnet zone, such that multiple analytes are simultaneously immunoassayed on spatially separated groups of magnetic beads within the microfluidic chip.

12. A microfluidic Western blot system including a microfluidic chip for immunoassay of analytes in a sample, the microfluidic chip comprising:

a sample well configured to hold the sample;

a sample channel in fluid communication with the sample well and configured to supply the sample to the system;

an injection channel in fluid communication with the sample channel, and the injection channel is configured to draw the sample from the sample well through the sample channel into the injection channel by applying a differential voltage between a sample well electrode corresponding to the sample well and an injection electrode disposed downstream of the injection channel;

a first separation electrode channel in fluid communication with the sample channel and the injection channel, the first separation electrode channel is configured to draw the sample from the injection channel into the first separation electrode channel by applying a differential voltage between the injection electrode and a first separation electrode disposed downstream of the first separation electrode channel;

a separation region in fluid communication with, and downstream of, the sample well, the sample channel, the injection channel, and the first separation electrode channel, wherein the sample channel, the injection channel, and the first separation electrode channel each terminate at a common, non-linear junction disposed at an upstream end of the separation region, the junction being spatially offset such that none of the three channels are collinear, the channels being electrically discrete and individually addressable by the sample-well electrode, the injection electrode, and the first separation electrode such that independent voltage control at the electrodes selectively routes a discrete plug of the sample among the channels without electrical crosstalk or unintended flow, and the injection electrode being positioned intermediate the sample well and the first separation electrode to establish a progressive voltage gradient through the junction during sample transfer;

a peak detection microfluidic channel disposed downstream of the separation region and upstream of a bead well, the peak detection microfluidic channel defining an optically accessible portion of the microfluidic chip configured to permit detection of fluorescent or luminescent optical signals from the separated analytes migrating from the separation region, the peak detection microfluidic channel enabling measurement of migration times and signal intensities of the separated analytes corresponding to analyte size and concentration and enabling generation of data for quantitative analysis of the separated analytes and for timing control of subsequent electrophoretic transfer toward the bead well;

a bead well in fluid communication with, and downstream of, the separation region, the bead well is configured to supply magnetic beads via a bead channel for attachment to the separated analytes to form protein-attached magnetic beads;

a magnetic holding region in fluid communication with, and downstream of, the separation region, the bead well, and the first separation electrode, the magnetic holding region being electrically isolated from the separation region to prevent electrophoretic migration during immunoassay incubation, and operably coupled to an electromagnet oriented to induce a magnetic field orthogonal to the electrophoretic flow direction within the magnetic holding region, the electromagnet is configured to fix the protein-attached magnetic beads in place within the magnetic holding region;

an antibody well in fluid communication with, and upstream of, the magnetic holding region, the antibody well is configured for flowing antibodies into the magnetic holding region via an immunoassay channel for binding to the protein-attached beads; and wherein:

the separation region is configured to draw the sample from the first separation electrode channel into the separation region and electrophoretically separate analytes in the sample within the separation region based on size and charge by applying a differential voltage between the first separation electrode and a second separation electrode disposed downstream of the separation region, the bead well is disposed upstream of the second separation electrode, the bead well is configured to supply the magnetic beads for attachment by applying a differential voltage between an electrode associated with the bead well and the second separation electrode, the magnetic holding region is disposed upstream of the second separation electrode such that the first and second separation electrodes are configured to move the sample from the separation region to the magnetic holding region by applying a differential voltage between the first and second separation electrode, and the antibody well is disposed upstream of the second separation electrode, the antibody well is configured to flow antibodies into the magnetic holding region by applying a differential voltage between an electrode associated with the antibody well and the second separation electrode.

13. The microfluidic chip of claim 12, wherein the antibody well is configured to hold either primary or secondary antibodies, and further comprising: a second antibody well configured to hold the other of primary or secondary antibodies, wherein the immunoassay channel is configured to supply primary antibodies or secondary antibodies to the magnetic holding channel for binding to the protein-attached magnetic beads.

14. The microfluidic chip of claim 12, further comprising a blocking buffer well and a detection reagent well, wherein the immunoassay channel is configured to supply blocking buffer or detection reagent to the magnetic holding channel for binding to the protein-attached magnetic beads.

15. The microfluidic chip of claim 12, further comprising a destain well operably coupled to, and downstream of, the separation region, the destaining well is configured to add destaining solution to the separated analytes in sample to remove detergent micelles, allowing visualization of protein peaks in the sample and reducing signal background upon detection.

16. The microfluidic chip of claim 12, further comprising a heating element operably coupled to the magnetic holding channel to control temperature for incubation within the magnetic holding channel.

17. The microfluidic chip of claim 12, wherein at least one internal surface of the separation region or the sample channel is coated with a hydrophilic polymer or zwitterionic surface layer to reduce protein adsorption and improve analyte migration uniformity during electrophoresis.

18. The microfluidic chip of claim 12, further comprising a calibration mode in which a reference sample containing molecular-weight standards is electrophoretically separated within the separation region to generate calibration peaks that establish migration-time and distance correlations for quantitative determination of analyte molecular weight.

* * * * *